United States Patent
Koch et al.

(10) Patent No.: US 6,997,183 B2
(45) Date of Patent: Feb. 14, 2006

(54) BREATHING GAS HUMIDIFIER SYSTEM FOR A PATIENT

(75) Inventors: Jochim Koch, Ratzeburg (DE); Marco Brombacher, Middelbeers (NL)

(73) Assignee: Dräger Medical AG & Co. KGaA, Lubeck (DE)

( * ) Notice: Subject to any disclaimer, the term of this patent is extended or adjusted under 35 U.S.C. 154(b) by 353 days.

(21) Appl. No.: 10/613,558

(22) Filed: Jul. 3, 2003

(65) Prior Publication Data

US 2004/0020487 A1    Feb. 5, 2004

(30) Foreign Application Priority Data

Jul. 31, 2002    (DE) .................................. 102 34 811

(51) Int. Cl.
*A61M 15/00* (2006.01)
*A61M 16/00* (2006.01)
*B01D 47/00* (2006.01)
*F02M 15/04* (2006.01)

(52) U.S. Cl. .......................... 128/203.17; 128/204.17; 128/203.16; 261/72.1; 261/142

(58) Field of Classification Search .......... 128/203.17, 128/203.16, 203.26, 204.17; 261/DIG. 65, 261/142, 72.1, 64.3
See application file for complete search history.

(56) References Cited

U.S. PATENT DOCUMENTS

| | | | | |
|---|---|---|---|---|
| 2,720,891 A | * | 10/1955 | Glasgow | 137/510 |
| 2,883,511 A | * | 4/1959 | Gooldy | 239/136 |
| 3,523,175 A | * | 8/1970 | Gygax | 392/402 |
| 4,060,576 A | * | 11/1977 | Grant | 261/130 |
| 4,172,105 A | * | 10/1979 | Miller et al. | 261/66 |
| 4,192,836 A | * | 3/1980 | Bartscher et al. | 261/142 |
| 4,195,044 A | * | 3/1980 | Miller | 261/142 |
| 4,225,542 A | * | 9/1980 | Wall et al. | 261/142 |
| 4,319,566 A | * | 3/1982 | Hayward et al. | 128/203.26 |
| 4,500,480 A | * | 2/1985 | Cambio, Jr. | 261/104 |
| 4,629,590 A | * | 12/1986 | Bagwell | 261/78.2 |
| 4,765,327 A | * | 8/1988 | Shim | 128/204.13 |
| 5,195,515 A | * | 3/1993 | Levine | 128/203.26 |
| 5,815,637 A | * | 9/1998 | Allen et al. | 392/400 |
| 5,916,493 A | * | 6/1999 | Miller | 261/154 |
| 6,031,968 A | * | 2/2000 | Holtmann | 392/402 |
| 6,244,576 B1 | * | 6/2001 | Tsai | 261/141 |
| 2004/0050386 A1 | * | 3/2004 | Levine | 128/203.16 |

* cited by examiner

FOREIGN PATENT DOCUMENTS

DE    296 17 077    2/1997

*Primary Examiner*—Henry Bennett
*Assistant Examiner*—Dinnatia Doster-Greene
(74) *Attorney, Agent, or Firm*—McGlew & Tuttle, PC

(57) ABSTRACT

A breathing gas humidifier system for a patient includes a replaceable, closed water reservoir (1) with stable pressure, provided for receiving a water reserve for the breathing gas humidifier system. An intermediate storage unit (4) with water is closed from the environment and is located under the water reservoir. The water reservoir (1) and the intermediate storage unit (4) have a valve (16, 14) each, with one of the valves cooperating with the other valve, so that there is a flow connection between the water reservoir (1) and the intermediate storage unit (4) only when the water reservoir (1) is received in a connector (2) of the intermediate storage unit (4). The intermediate storage unit (4) is connected via a water connection line (5) located below the water level to a heated evaporator chamber (7), which opens above the water evaporating at the boiling point into the breathing gas line to a patient. A gas pressure equalizing line (12) is located between the heated evaporator chamber (7) and the intermediate storage unit (4).

20 Claims, 3 Drawing Sheets

BREATHING GAS HUMIDIFIER SYSTEM FOR A PATIENT

FIELD OF THE INVENTION

The present invention pertains to a breathing gas humidifier system for a patient with the system including a water reservoir and a flow connection.

BACKGROUND OF THE INVENTION

Breathing gas humidifier systems are preferably used in the artificial respiration of patients, and respirators with a fan generating a continuous respiration pressure are also increasingly used for respiration in the home, especially also for the treatment of sleep apnea. To prevent the respiratory tract from drying out, there is a need for breathing gas humidifier systems, which have a simple design and can be operated in a simple manner.

The drawback of the breathing gas humidifier systems known so far, as described, e.g., in DE 296 17 077 U1, is that to equalize the pressure in the apparatus, the water fed in from sterile water containers has a direct connection to the environment, through which germs may spread over time. Moreover, breathing pressure cannot build up in the breathing gas line to the patient when this prior-art humidifier system is used for respirators with continuous respiration pressure, because there is a pressure equalization with the environment in the area of the water distributor.

SUMMARY OF THE INVENTION

The object of the present invention is to provide a breathing gas humidifier system, which has a simple design, can be operated in a simple manner and makes possible germ-free operation even in combination with a respirator generating a continuous overpressure.

According to the invention, a breathing gas humidifier system for a patient is provided with a replaceable, closed water reservoir with stable pressure provided for receiving a water reserve for the breathing gas humidifier system. An intermediate storage unit is provided with water, which is closed from the environment. The intermediate storage unit is located under the water reservoir. The water reservoir and the intermediate storage unit have a valve each, with one of the valves cooperating with the other valve so that there is a flow connection between the water reservoir and the intermediate storage unit only when the water reservoir is received in a connector of the intermediate storage unit. The intermediate storage unit is connected via a water connection line located below the water level to a heated evaporator chamber, which opens above the water evaporating at the boiling point into the breathing gas line to a patient. A gas pressure equalizing line is located between the heated evaporator chamber and the intermediate storage unit.

The water reservoir and the intermediate storage unit valves or first and second valves may each be nonreturn valves with a corresponding first and second restoring spring. These valves may be opened by actuating a plunger at one of the valves.

The evaporator chamber may have a shield around which medium can flow as around a flow obstacle, in front of the outlet into the breathing gas line to the patient. A respirator generating a continuous respiration pressure may be connected to the breathing gas line.

An electrocapacitive humidity sensor may be arranged in a mixing chamber of the breathing gas humidifier system, so that the heating line of the heater is set after the comparison of the measured values for the breathing gas humidity with preset set points by means of a electronic unit.

The water connection line preferably has a diameter of 1 mm to 2.5 mm. The water reservoir may consists of polyethylene or polypropylene, especially preferably from polyethylene terephthalate (PET), a polycarbonate (PC) or an ethylene/propylene copolymer (PEP).

One essential advantage of the present invention is that the breathing gas humidifier system including the water reserve and the intermediate storage unit is closed from the environment, so that the growth of germs is practically ruled out. Another advantage for the patient arises from the constant water level in the heated evaporator chamber, so that a uniform amount of water is generated over time once the heater has been turned on.

The replaceable, closed water reservoir with stable pressure and the intermediate storage unit of the breathing gas humidifier system preferably have a nonreturn valve each at the connection site formed by a connector, which nonreturn valves cooperate during the replacement of the water reservoir such that there is a flow connection between the water reservoir and the intermediate storage unit only when the water reservoir is taken up in the connector of the intermediate storage unit, and the valves are otherwise closed.

One exemplary embodiment of the present invention will be explained below on the basis of the figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which the preferred embodiment of the invention is illustrated.

DESCRIPTION OF THE PREFERRED EMBODIMENT

Figure 1:
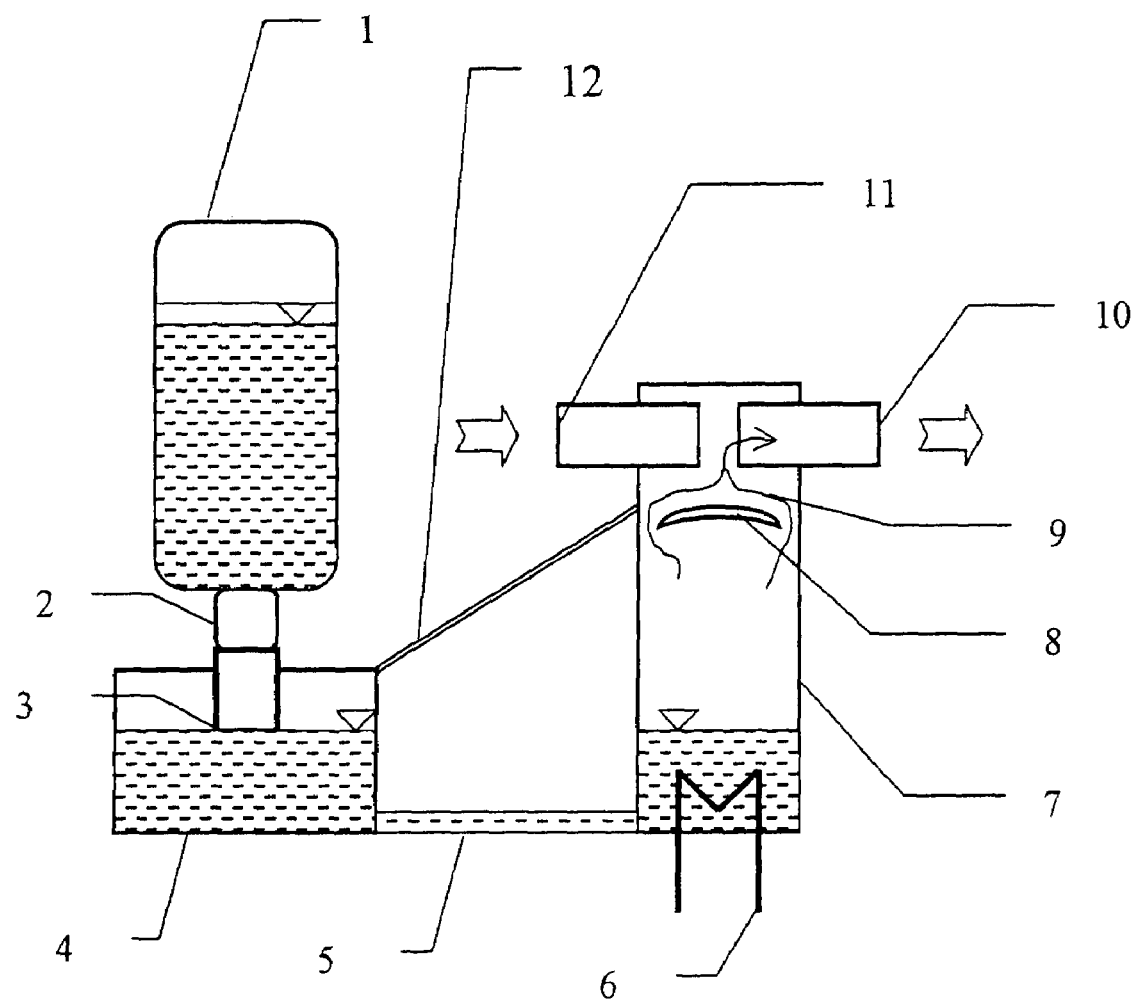
FIG. 1 is a schematic view of the breathing gas humidifier system according to the invention.

Referring to the drawings in particular, the invention provides a system in which sterile water is kept ready in a replaceable, closed water reservoir 1 with stable pressure such as according to FIG. 1. The water reservoir 1 is preferably made of a robust and transparent plastic such as PET, PC or PEP in order to make possible reliable handling and visual checking of the water level. An amount of water of about 300 to 500 mL is needed for an operating time of about 8 to 10 hours for the typical use in respiration at home. The water reservoir 1 is connected via the connector 2 to the intermediate storage unit 4.

Figure 2:
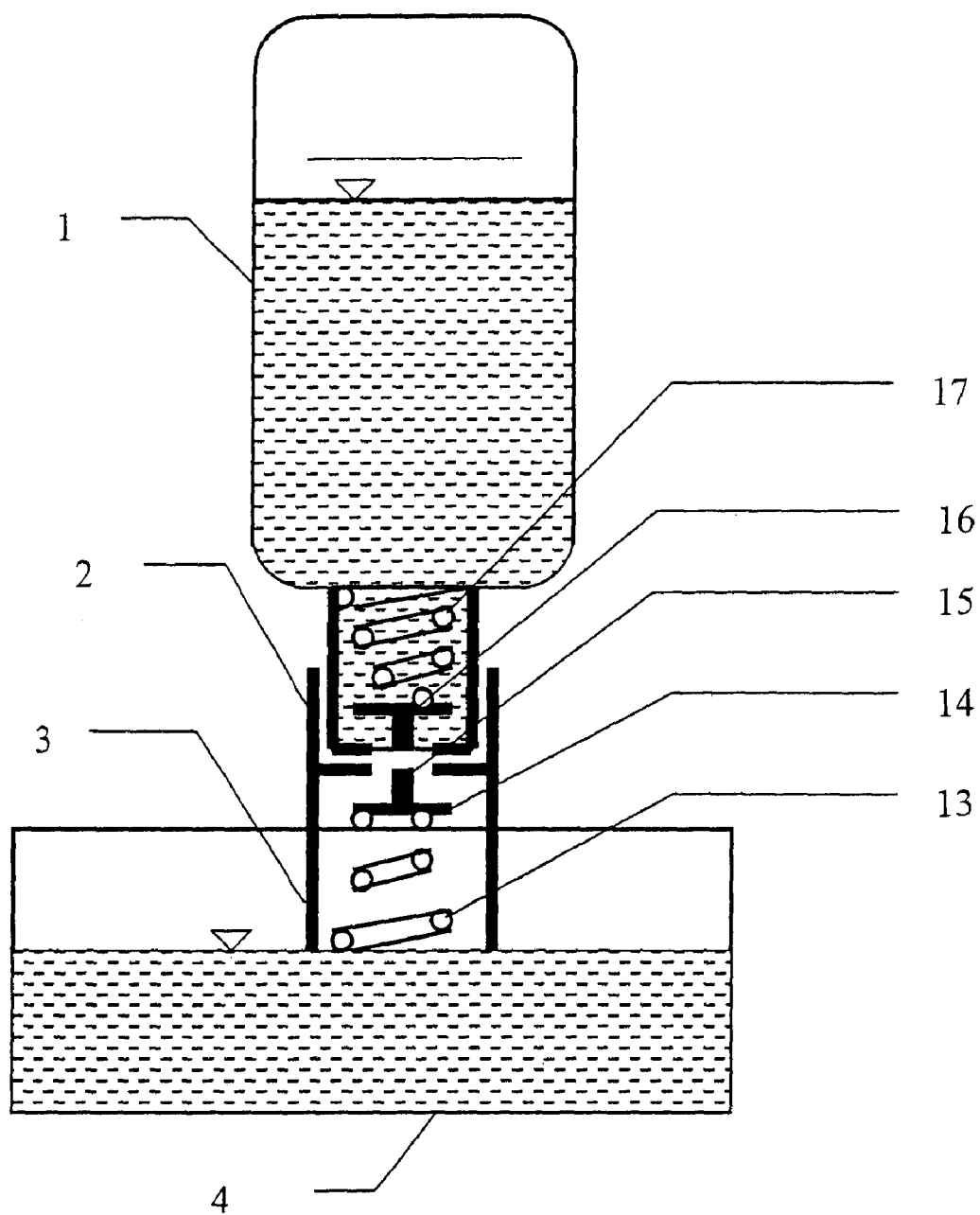
FIG. 2 is a schematic view of the connection between the water reservoir and the intermediate storage unit according to the invention.

FIG. 2 shows the details of the connector 2. When the water reservoir 1 is inserted into the connector 2 from the top, both the first valve 16 with the first restoring spring 17 of the water reservoir 1 and the second valve 14 with the second restoring spring 13 of the intermediate storage unit 4 are actuated and opened via the plunger 15. Water can thus run from the water reservoir 1 into the intermediate storage unit 4 of the humidifier system until the water level has risen to the extent that the channel 3 of the connector 2 is closed and no air can flow into the water reservoir 1. When the water reservoir 1 is removed, both the water reservoir and the intermediate storage unit 4 are again closed, so that no more water escapes from the water reservoir 1 and the breathing gas humidifier system does not supply any more humidity after the evaporation of the residual amount of water, but the pressure in the breathing gas line in a connected respirator is preserved. The water is sent into the evaporator chamber 7 via a water connection line 5 with a diameter of about 1 mm to 2.5 mm. The heater 6 is provided in the evaporator chamber 7. The heater 6 supplies the necessary heating energy to heat the water and to boil and evaporate it. The water vapor rises in the evaporator chamber 7 and is deflected by the shield 8, so that water drops or bubbles will not enter the inspiration gas in the breathing gas line. The water vapor is sent over the path 9 into the outlet spout 10 and is mixed there with the inspiration gas to the patient, which arrives from the inlet spout 11. Pressure equalization is established between the outlet spout 10 and the intermediate storage unit 4 acting as a water level regulator via the gas pressure equalizing line 12. The same pressure prevails in the outlet spout 10 as in the breathing gas line. If more water runs in from the water reservoir 1, the air flowing after it as a result is fed in via this gas pressure equalizing line 12.

The narrow water connection line 5 with a diameter of about 1 mm to 2.5 mm, which extends below the water level in the intermediate storage unit 4 and in the evaporator chamber 7 between the boiling water in the evaporator chamber 7 and the cold water supply from the water reservoir 1 acts as a heat-insulating connection, so that no convection can develop and the water in the intermediate storage unit 4 is not heated, so that the water in the water reservoir 1 and the air contained in it will not be heated and will not expand and thus it will not deliver too much water into the evaporator chamber 7 as a result.

Figure 3:
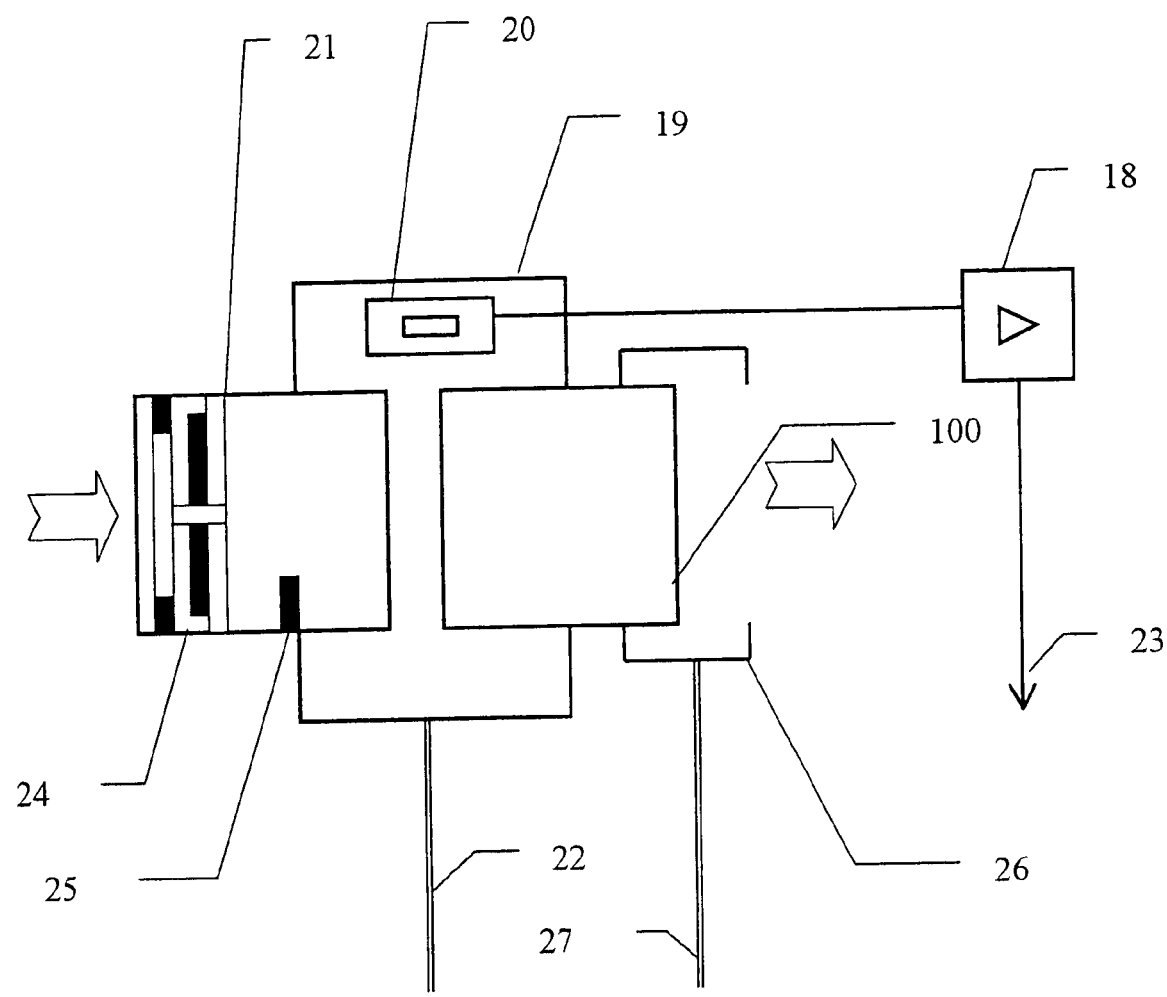
FIG. 3 is a schematic view of the arrangement of a humidity sensor in the breathing gas line for use with a breathing gas humidifier system.

While the simplest mode of operation of the humidifier system according to FIG. 1 is the continuous heating of the evaporator chamber 7 at a water evaporation rate that is constant over time, a mode of operation is explained in FIG. 3 as a function of the measured breathing gas humidity at the entry into the breathing gas line to the patient. The inspiration tract 100 to the patient joins the line 21, which is located at the outlet of the breathing gas humidifier system. Breathing gas from the respirator has already mixed there with evaporated humidity. A gap, which is surrounded by a mixing chamber 19, is located between the line 21 and the inspiration tract 100. A humidity sensor 20, especially an electrocapacitive humidity sensor, is located in this mixing chamber 19 in the upper part, and the humidity sensor is arranged such that it is heated by the housing of the breathing gas humidifier system or the waste heat of the electrical components belonging to it such that it is warmer than the humid breathing gas and is protected from condensation. A steady bypass flow via a narrow channel 22 ensures the ventilation of the chamber 19, so that the humidity sensor 20 always detects the current humidity level in the breathing gas. The measured signal of the humidity sensor 20 is sent to an electronic unit 18, where the measured signal is compared with preset set points, and the heating output 23 of the heater 6 (FIG. 1) is adjusted correspondingly. A nonreturn valve 24, which is opened by the breathing gas flow from the respirator, is located at the inlet of the breathing gas humidifier system. When the breathing gas flow is shut off, the nonreturn valve 24 closes automatically and prevents the water vapor from flowing from the breathing gas humidifier system into the respirator and from condensing there. Furthermore, a water threshold 25 is present, which prevents condensate that may be present there from reaching the respirator. Another water trap 26 is provided at the end of the housing, so that no condensate can enter the breathing gas line and be collected or flow off via the channels 22 and 27.

While specific embodiments of the invention have been shown and described in detail to illustrate the application of the principles of the invention, it will be understood that the invention may be embodied otherwise without departing from such principles.

What is claimed is:

1. A breathing gas humidifier system comprising:
   a replaceable and closed water reservoir with stable pressure, said water reservoir being provided for receiving a water reserve for the breathing gas humidifier system;
   an intermediate storage unit with water, said intermediate storage being closed from the environment and being located under the water reservoir and having a connector;
   a reservoir valve associated with said water reservoir;
   an intermediate storage unit valve associated with said intermediate storage unit, said reservoir valve and said intermediate storage unit valve cooperating to provide a water flow connection between said water reservoir and said intermediate storage unit only when the water reservoir is received in said connector;
   a heated evaporator chamber with an outlet connected to a breathing gas line and to a patient;
   a water connection line located below a water level of said intermediate storage unit, said intermediate storage unit being connected via said water connection line to said heated evaporator chamber, said outlet opening above water in said heated evaporator chamber, the water evaporating at the boiling point passing via the outlet into the breathing gas line to the patient; and
   a gas pressure equalizing line located between said heated evaporator chamber and said intermediate storage unit.

2. A breathing gas humidifier system in accordance with claim 1, further comprising: a first restoring spring; a second restoring spring; and a plunger wherein said reservoir valve and said intermediate storage unit valve are each nonreturn valves cooperating with said first restoring spring and said second restoring spring respectively, wherein said reservoir valve and said intermediate storage unit valve are opened by actuating said plunger at one of said reservoir valve and said intermediate storage unit valve.

3. A breathing gas humidifier system in accordance with claim 1, wherein said evaporator chamber has a shield, evaporated medium flowing around said shield into the breathing gas line to the patient with said shield acting as a flow obstacle in front of said outlet.

4. A breathing gas humidifier system in accordance with claim 2, wherein said evaporator chamber has a shield, evaporated medium flowing around said shield into the breathing gas line to the patient with said shield acting as a flow obstacle in front of said outlet.

5. A breathing gas humidifier system in accordance with claim 1, further comprising a respirator generating a continuous respiration pressure connected to the breathing gas line.

6. A breathing gas humidifier system in accordance with claim 2, further comprising a respirator generating a continuous respiration pressure connected to the breathing gas line.

7. A breathing gas humidifier system in accordance with claim 1, further comprising an electronic unit connected to the heater via a heater line and an electrocapacitive humidity sensor arranged in a mixing chamber of the breathing gas humidifier system, said electronic unit setting a value of a setting signal for the heating line of the heater after the comparison of the measured values for the breathing gas humidity with preset set points.

8. A breathing gas humidifier system in accordance with claim 1, wherein the water connection line has a diameter of 1 mm to 2.5 mm.

9. A breathing gas humidifier system in accordance with claim 1, wherein the water reservoir consists of polyethylene or polypropylene.

10. A breathing gas humidifier system in accordance with claim 9, wherein the water reservoir consists of polyethylene terephthalate (PET), a polycarbonate (PC) or an ethylene/propylene copolymer (PEP).

11. A breathing gas humidifier system comprising:
  a water reservoir enclosure for maintaining a stable pressure, said water reservoir enclosure receiving water as a reserve for the breathing gas humidifier system;
  an intermediate storage unit for receiving water from said reservoir enclosure, said intermediate storage being closed from the environment and being located below a level of said water reservoir enclosure and having a connector;
  a reservoir valve associated with said water reservoir;
  an intermediate storage unit valve associated with said intermediate storage unit, said reservoir valve and said intermediate storage unit valve cooperating to provide a flow connection between said water reservoir and said intermediate storage unit to provide water up to a water level in said intermediate storage unit only when the water reservoir is received in said connector;
  an evaporator chamber with an outlet connected to a breathing gas line and to a patient;
  a heater disposed in said evaporator chamber;
  a water connection line located below a water level of said intermediate storage unit, said intermediate storage unit being connected via said water connection line to said heated evaporator chamber, said outlet opening being above a water level in said heated evaporator chamber, whereby the water evaporates at the boiling point passing to the outlet and into the breathing gas line to the patient; and
  a gas pressure equalizing line providing a gas pressure equalizing connection between said heated evaporator chamber and said intermediate storage unit.

12. A breathing gas humidifier system in accordance with claim. 11, further comprising: a first restoring spring; a second restoring spring; and a plunger wherein said reservoir valve and said intermediate storage unit valve are each nonreturn valves cooperating with said first restoring spring and said second restoring spring respectively, wherein said reservoir valve and said intermediate storage unit valve are opened by actuating said plunger at one of said reservoir valve and said intermediate storage unit valve.

13. A breathing gas humidifier system in accordance with claim 11, wherein said evaporator chamber has a shield, evaporated medium flowing around said shield into the breathing gas line to the patient with said shield acting as a flow obstacle in front of said outlet.

14. A breathing gas humidifier system in accordance with claim 12, wherein said evaporator chamber has a shield, evaporated medium flowing around said shield into the breathing gas line to the patient with said shield acting as a flow obstacle in front of said outlet.

15. A breathing gas humidifier system in accordance with claim 11, further comprising a respirator generating a continuous respiration pressure connected to the breathing gas line.

16. A breathing gas humidifier system in accordance with claim 12, further comprising a respirator generating a continuous respiration pressure connected to the breathing gas line.

17. A breathing gas humidifier system in accordance with claim 11, further comprising: and electronic unit connected to the heater via a heater line and an electrocapacitive humidity sensor arranged in a mixing chamber of the breathing gas humidifier system, said electronic unit setting a value of a setting signal for the heating line of the heater after the comparison of the measured values for the breathing gas humidity with preset set points.

18. A breathing gas humidifier system in accordance with claim 11, wherein the water connection line has a diameter of 1 mm to 2.5 mm.

19. A breathing gas humidifier system in accordance with claim 11, wherein the water reservoir consists of polyethylene or polypropylene.

20. A breathing gas humidifier system in accordance with claim 19, wherein the water reservoir consists of polyethylene terephthalate (PET), a polycarbonate (PC) or an ethylene/propylene copolymer (PEP).

* * * * *